(12) United States Patent
Greter et al.

(10) Patent No.: US 7,160,273 B2
(45) Date of Patent: Jan. 9, 2007

(54) SUCTION PUMP

(75) Inventors: Andy Greter, Steinhausen (CH);
Hansruedi Kuenzler, Mettmenstetten (CH); Brian H. Silver, Cary, IL (US)

(73) Assignee: Medela AG, Baar (CH)

( * ) Notice: Subject to any disclaimer, the term of this patent is extended or adjusted under 35 U.S.C. 154(b) by 205 days.

(21) Appl. No.: 10/362,981

(22) PCT Filed: Aug. 28, 2001

(86) PCT No.: PCT/CH01/00524

§ 371 (c)(1),
(2), (4) Date: Jul. 7, 2003

(87) PCT Pub. No.: WO02/17992

PCT Pub. Date: Mar. 7, 2002

(65) Prior Publication Data

US 2004/0024360 A1     Feb. 5, 2004

(30) Foreign Application Priority Data

Aug. 28, 2000 (EP) ................... 00118590

(51) Int. Cl.
*A61M 1/00* (2006.01)
*A61M 27/00* (2006.01)

(52) U.S. Cl. ..................... 604/319; 604/317
(58) Field of Classification Search ................ 604/313, 604/315–316, 540–544, 317, 319, 35
See application file for complete search history.

(56) References Cited

U.S. PATENT DOCUMENTS

| 3,084,691 | A | | 4/1963 | Stoner | |
|---|---|---|---|---|---|
| 3,572,979 | A | * | 3/1971 | Morton | 623/3.21 |
| 3,777,742 | A | * | 12/1973 | Aumiller et al. | 600/431 |
| 4,127,115 | A | * | 11/1978 | Franetzki | 600/538 |
| 4,256,106 | A | * | 3/1981 | Shoor | 604/411 |
| 4,698,060 | A | * | 10/1987 | D'Antonio et al. | 604/320 |
| 4,930,997 | A | * | 6/1990 | Bennett | 417/410.1 |
| 5,419,687 | A | | 5/1995 | Adahan | |
| 5,466,229 | A | | 11/1995 | Elson et al. | |
| 5,662,627 | A | | 9/1997 | Say | |
| 6,059,803 | A | * | 5/2000 | Spilman | 606/162 |
| 6,135,980 | A | * | 10/2000 | Vu | 604/73 |
| 6,517,511 | B1 | * | 2/2003 | Yao | 604/35 |
| 6,855,109 | B1 | * | 2/2005 | Obata et al. | 600/158 |
| 2003/0181786 | A1 | * | 9/2003 | Heimberger | 600/159 |

FOREIGN PATENT DOCUMENTS

| EP | 1184043 A1 * | 3/2002 |
|---|---|---|
| GB | 2307180 A * | 5/1997 |
| WO | WO 9910024 A1 * | 3/1999 |
| WO | 00/15277 A2 | 3/2000 |

OTHER PUBLICATIONS

Definitions related to "separate" and "accumulator" from various online dictionaries.*

* cited by examiner

*Primary Examiner*—Tatyana Zalukaeva
*Assistant Examiner*—Keshia Gibson
(74) *Attorney, Agent, or Firm*—Baniak Pine & Gannon

(57) ABSTRACT

The suction pump is essentially comprised of three separate pump parts, namely of a drive unit located inside a main casing (1), of a collecting reservoir (8) and of a valve block (6), which is arranged directly between the casing (1) and reservoir, whereby these parts can be easily coupled to one another in a manner that enables them to be detached.

9 Claims, 2 Drawing Sheets

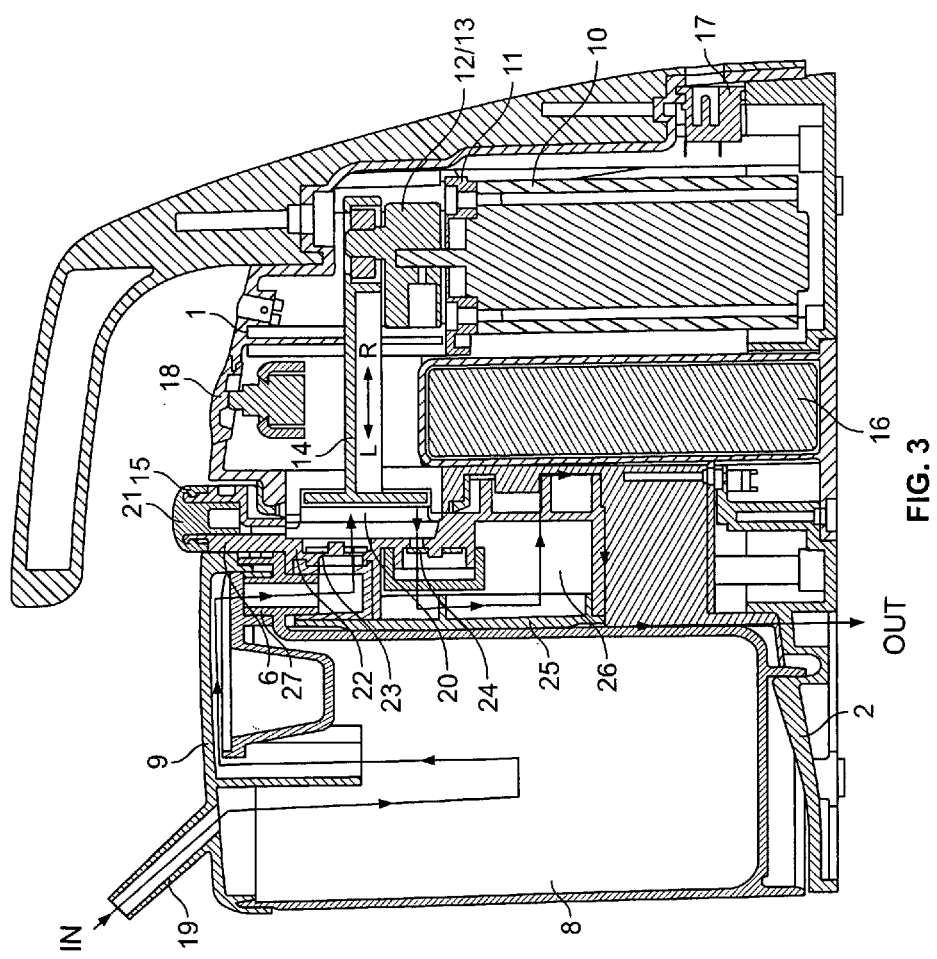

SUCTION PUMP

Figure 1:
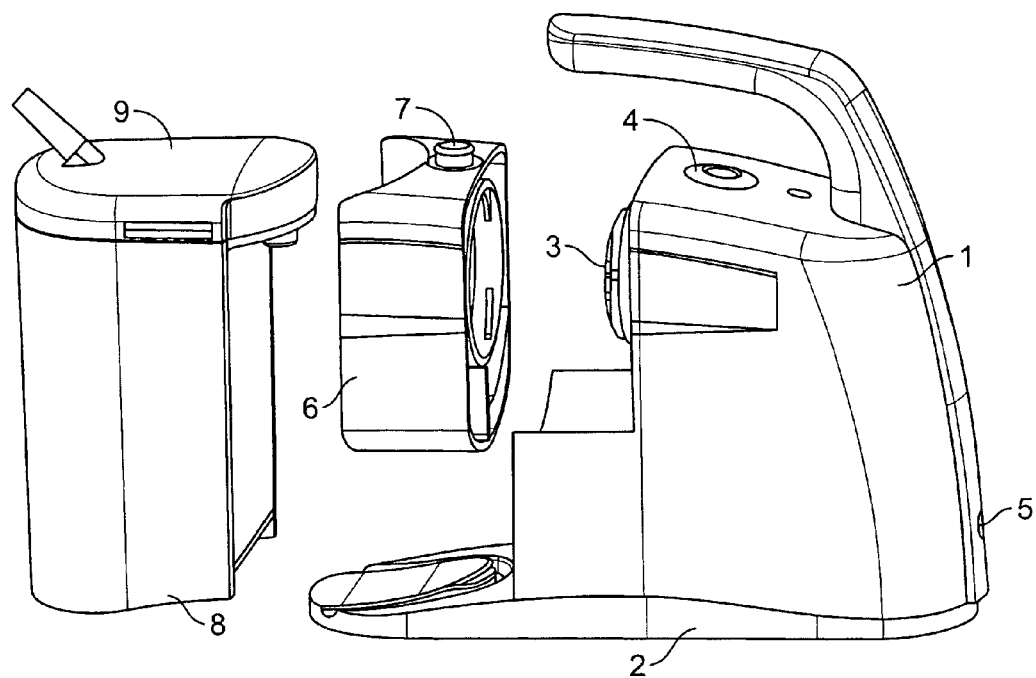

The present invention relates to a suction pump for medical applications, specifically a pump for sucking off secretions, with a collecting reservoir for material to be sucked off, a valve block for a alternating connection of the pump chamber through corresponding valves to the collecting reservoir for a production of a vacuum in latter or a blowing off conduit resp., depending from the direction of movement of a membrane pump plunger, and a driving unit of the membrane pump plunger.

The nowadays known suction pumps of this kind have the drawback, that except the demountable collecting reservoir the cleaning of the other pump parts is complicated and difficult, because specifically great care must be taken in order to prevent a liquid (washing liquid, rests of secretion) from penetrating into the driving unit.

Object of the present invention has been to provide a suction pump which having a as simple as possible design can be easily assembled and again disassembled for cleaning purposes without any special knowledge (no hose connections). The manipulating shall be as easy as possible (one button On/Off) and the collecting reservoir shall be able to be washed after its emptying in the washing machine, e.g. a dishwasher. Also the other pump parts, that is valve block and driving unit, which due to a special overflow design of the collecting reservoir are not subject to a contamination, shall if necessary be able to be washed without a detrimental influence on their function properties.

This object is solved by a suction pump of the kind defined above in accordance with the invention by the features of the characterizing portion of claim 1.

The various pump parts are, thereby, preferably arranged at a common base plate by means of plug in and/or snap on connections.

In the following, the invention is explained somewhat more in detail with reference to a embodiment illustrated in the drawing.

Figure 2:
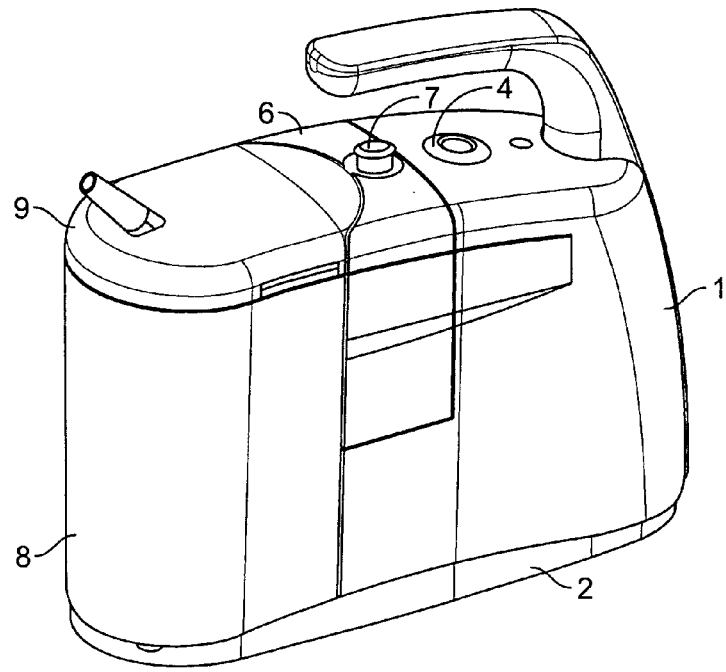

There is shown in:

FIG. 1 purely schematically a suction pump to be formed of three main parts;

FIG. 2 a suction pump assembled from the three main parts according to FIG. 1; and FIG. 3 a longitudinal section through the suction pump according to FIG. 2 on a somewhat enlarged scale.

FIG. 1 of the drawing illustrates the three main parts of the suction pump, namely the main housing 1 with the mounted motor, pump drive and possibly an accumulator (these mounting parts are illustrated in FIG. 3), which is plugged onto a base plate 2, whereby the membrane 3 of a membrane pump plunger (see FIG. 3), the main switch 4 (On/Off) as well as a electric power connection 5 are illustrated, furthermore a valve block 6 with overflow chamber (FIG. 3) and vacuum setting button 7 (e.g. two positions) and finally a reusable collecting reservoir 8 with cover 9 placed thereupon.

The main parts of the suction pump illustrated in FIG. 1 can be assembled easily (plugging and snap on connections) and obviously be in the same manner easily disassembled (for cleaning purposes). The valve block 6 cones, thereby, to lie directly between the main housing 1 and the exchangeable collecting reservoir 8 such as illustrated by FIG. 2. The main parts are preferably plugged onto the base plate 2.

The concept of the design in accordance with the invention can be best seen at the cross section according to FIG. 3.

In the main housing 1 an electromotor 10 (e.g. a 12V—direct current motor) is flanged onto a plate 11 and serves for the driving of an eccentric 12 (with additional unbalance 13). The eccentric 12 serves as drive for the pump plunger 14 which is provided with a membrane 15 (e.g. a spray coated membrane) and serves in operation for the production of a desired vacuum. An accumulator 16 is also present in the main housing 1 which is plugged onto a base plate 2. A power supply from the outside proceeds through a connecting bushing 17 (12V—direct current for the supply of the accumulator 16 or for a direct supply of the motor 10). Finally, a press button switch 18 (On/Off) is arranged on the upper side of the housing 18.

Also plugged onto the base plate 2, at the left side, is the exchangeable, reusable collecting reservoir 8 for the material to be sucked off (e.g. secretion) with reservoir cover 9. The material to be sucked off by vacuum produced in the reservoir 8 enters the reservoir 8 through a conduit hose (not illustrated) to be connected to the stub 19.

As third separate main part a valve block 6 is inserted between the collecting reservoir 8 and main housing 1, whereby it is coupled releasable by suitable connectors to the reservoir 8 and the housing 1. Because the actual pump chamber 20 is located between the valve block 6 and the membrane pump plunger 14 with the membrane 15 located at its front end arranged in the main chamber 1, this chamber 20 is connected to a device for setting the desired vacuum (vacuum setting button 21 with e.g. two different positions).

Automatically operating valves 23 and 24, resp. are arranged in a wall 22 of the valve block 6: When the plunger 14 and membrane 15, resp. moves in the direction R, a vacuum is produced and air is sucked out of the reservoir 8 through the valve 23 which opens (in order to produce a vacuum in the receiving reservoir). At the pushing movement of the plunger 14 and the membrane 15, resp. in the direction L the valve 23 closes and the air sucked into the pump chamber 20 is expelled through the valve 24 which opens, this into a chamber 26 closed by means of a cover 25 which is in communication with the environment through free channels between the pump parts which are connected to each other (Off).

The connection between collecting reservoir 8 and valve block 6 proceeds through a stub 27 located at a high spot which in a emergency forms also a overflow for the reservoir 8. Due to this specific design, liquid which possibly enters the valve block 6 can not detrimentally influence the driving unit of the pump.

The individual pump parts 1, 6 and 8 can be assembled and disassembled in a easiest way which renders their cleaning to be very easy and without any problems (collecting reservoir 8 and valve block can be cleaned in a dishwasher).

The invention claimed is:

1. A suction pump for medical applications, specifically a pump for sucking off secretions, with a collecting reservoir for material to be sucked off, a valve block for an alternating connection of a pump chamber through corresponding valves for a production of a vacuum in latter or a blowing off circuit respectively, depending from a direction of movement of a membrane pump plunger, and a driving unit of the membrane plunger, characterized in that the collecting reservoir, valve block and driving unit are housed separately and are releasably coupled to each other for operation of the pump, whereby the valve block comes to lie directly between the collecting reservoir and driving unit and the membrane pump plunger located in the driving unit cooperates at a front end of the plunger with a membrane which is arranged sealed against an inside of the driving unit, and exposed towards the environment, and the pump chamber is located between valve block and driving unit and is defined by a wall of the valve block provided with the valves and a wall of the driving unit or membrane, respectively.

2. The suction pump according to claim 1, characterized in that the releasably coupled pump parts are arranged on a common plate.

3. The suction pump according to claim 1 or 2, characterized in that releasable connection between the pump parts proceeds through plug in and/or snap on connections.

4. The suction pump according claim 1, characterized in that the valve block communicates in an assembled state with two compartments separated from each other, comprising a first compartment which can be connected to the collecting reservoir and can be connected through a suction valve to the pump chamber, and a second compartment, which connects the pump chamber through an outlet valve to a blow-off circuit.

5. The suction pump according to claim 1, wherein the pump parts can be easily assembled and again disassembled for cleaning purposes without any special knowledge and without hose connections.

6. The suction pump according to claim 1, wherein the driving unit comprises a main housing, a pump drive and possibly an accumulator, wherein the main housing is plugged onto a base plate.

7. The suction pump according to claim 1, wherein the valve block comprises a vacuum setting button for adjustment of the desired vacuum.

8. The suction pump according to claim 1, wherein the collecting reservoir comprises a cover placed thereupon.

9. The suction pump according to claim 1, wherein the connection between collecting reservoir and valve block proceeds through a stub located at a high spot which in an emergency forms also an overflow for the reservoir.

* * * * *